United States Patent
Zoabi et al.

(10) Patent No.: US 12,419,693 B2
(45) Date of Patent: Sep. 23, 2025

(54) APPLYING ABLATION SIGNALS TO BOTH SIDES OF TISSUE

(71) Applicant: BIOSENSE WEBSTER (ISRAEL) LTD., Yokneam (IL)

(72) Inventors: Akram Zoabi, Haifa (IL); Sigal Altman, Ramat Hashofet (IL); Meytal Segev, Haifa (IL); Fady Massarwa, Baka al Gharbiyya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 699 days.

(21) Appl. No.: 17/844,265

(22) Filed: Jun. 20, 2022

(65) Prior Publication Data

US 2023/0404677 A1    Dec. 21, 2023

(51) Int. Cl.
| | |
|---|---|
| *A61B 34/20* | (2016.01) |
| *A61B 18/14* | (2006.01) |
| *A61B 18/00* | (2006.01) |
| *A61B 34/00* | (2016.01) |
| *A61B 34/10* | (2016.01) |

(52) U.S. Cl.
CPC .......... *A61B 34/20* (2016.02); *A61B 18/1492* (2013.01); *A61B 2018/00351* (2013.01); *A61B 2018/00357* (2013.01); *A61B 2018/00363* (2013.01); *A61B 2018/00577* (2013.01); *A61B 2034/107* (2016.02); *A61B 2034/252* (2016.02)

(58) Field of Classification Search
CPC ........ A61B 2034/107; A61B 2034/252; A61B 2018/00351; A61B 2018/00357; A61B 2018/00363

See application file for complete search history.

(56) References Cited

U.S. PATENT DOCUMENTS

| | | |
|---|---|---|
| 5,391,199 A | 2/1995 | Ben Haim |
| 6,239,724 B1 | 5/2001 | Doron |
| 6,332,089 B1 | 12/2001 | Acker |
| 6,484,118 B1 | 11/2002 | Govari |
| 6,618,612 B1 | 9/2003 | Acker |
| 6,690,963 B2 | 2/2004 | Ben Haim |
| 10,588,692 B2 | 3/2020 | Saba et al. |
| 10,842,572 B1 | 11/2020 | Viswanathan |
| 2002/0065455 A1 | 5/2002 | Ben Haim |
| 2003/0120150 A1 | 6/2003 | Govari |
| 2004/0068178 A1 | 4/2004 | Govari |
| 2009/0093806 A1 | 4/2009 | Govari |

(Continued)

FOREIGN PATENT DOCUMENTS

WO    WO9605768 A1    2/1996

OTHER PUBLICATIONS

International Search Report for corresponding PCT Appln. No. PCT/IB2023/055625 dated Sep. 21, 2023.

*Primary Examiner* — Sean W Collins

(57) ABSTRACT

A system includes a display and a processor. The display is configured to display at least a map of an organ having tissue including first and second surfaces that are facing one another. The processor is configured to: (i) receive a first position of a first lesion formed by ablating the first surface, (ii) calculate on the second surface, a second position that is facing the first position, and (iii) display, over the map, a marker indicative of the second position for guiding a user to produce in the tissue a second lesion facing the first lesion.

18 Claims, 2 Drawing Sheets

(56) References Cited

U.S. PATENT DOCUMENTS

| | | |
|---|---|---|
| 2009/0138007 A1 | 5/2009 | Govari |
| 2012/0209260 A1* | 8/2012 | Lambert ............ A61B 18/1492 606/41 |
| 2015/0342662 A1* | 12/2015 | Bustan .................. A61B 34/10 606/34 |
| 2021/0085387 A1 | 3/2021 | Amit |
| 2024/0407836 A1* | 12/2024 | Girouard ............ A61B 18/1233 |

* cited by examiner

APPLYING ABLATION SIGNALS TO BOTH SIDES OF TISSUE

FIELD OF THE DISCLOSURE

The present disclosure relates generally to medical devices, and particularly to methods and systems for assisting the application of ablation signals to both sides of tissue.

BACKGROUND OF THE DISCLOSURE

Various techniques for visualizing catheters and tissue in question have been published.

For example, U.S. Patent Application Publication No. 2021/0085387 describes a system including an interface and a processor. The interface is configured to receive data that characterizes an initial ablation operation applied to a region of a heart of a patient. The processor is configured to automatically specify, based on the received data, if found required, a complementary ablation operation to be applied to the region.

BRIEF DESCRIPTION OF THE DRAWINGS

The present disclosure will be more fully understood from the following detailed description of the examples thereof, taken together with the drawings in which.

DETAILED DESCRIPTION OF EXAMPLES

Overview

Figure 1:
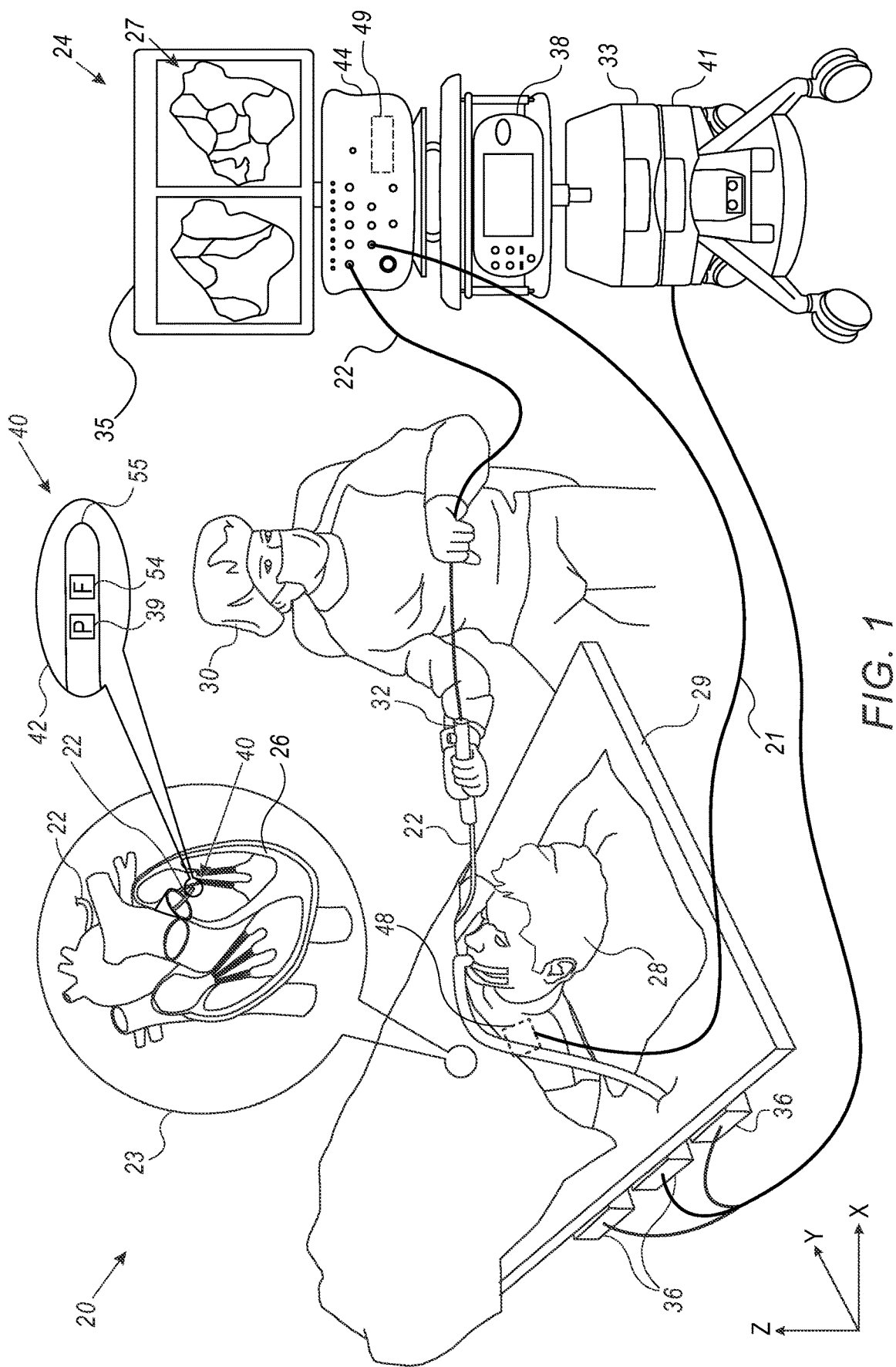
FIG. 1 is a schematic, pictorial illustration of a catheter-based tracking and ablation system, in accordance with an example of the present disclosure.

Some tissue ablation procedures, such as ablation of heart pericardium for treating arrhythmias, require the formation of one or more lesions through the entire thickness of the pericardium. In some cases, using an ablation catheter for applying ablation signals to one side of the pericardium, e.g., to the endocardium or epicardium, is sufficient to form a lesion through the entire thickness of the pericardium. In other cases, however, the lesion formed in response to applying the ablation signals to one side (e.g., to the endocardium) is incomplete, and does not terminate the arrhythmia in the treated heart. In such cases, the physician has to navigate the ablation catheter for applying additional ablation signals to the epicardium at positions that are facing the lesions formed on the endocardium, but determining such positions may be difficult due to the three-dimensional (3D) structure of the heart.

Examples of the present disclosure that are described hereafter provide improved techniques for displaying, to a user, annotations of: (i) lesions formed on a first side of tissue, and (ii) suggested positions at a second opposite side of the tissue, which are facing the lesions formed on the first side.

In some examples, a system for treating arrhythmia comprises a suitable catheter having one or more ablation electrodes and one or more position sensors configured to produce signals indicative of the catheter position in a predefined XYZ coordinate system.

In some examples, the system comprises a display, which is configured to display at least a map of an organ (e.g., patient heart) having tissue comprising first and second surfaces that are facing one another, and are also facing fluids of the organ. For example, in the heart, the first and second sides of the pericardium comprise the endocardium and the epicardium, respectively. Given sections of the endocardium and epicardium are facing one another, wherein the endocardium is also facing blood being pumped through the heart, and the epicardium is facing fluids surrounding the heart.

In some examples, the system comprises a processor, which is configured to receive one or more first positions of one or more first respective lesions formed on the endocardium. The processor is configured to calculate on the epicardium surface, one or more second positions that are facing the respective one or more first position of the first lesions formed on the endocardium. In the present example, the processor is configured to compute a projection of the one or more first positions on the surface of the epicardium. In the context of the present disclosure and in the claims, the term "projection" refers to the shortest distance between the respective first and second positions on the endocardium and epicardium, respectively. Note that the projection for each pair of first and second positions, may be carried out at any suitable direction in XYZ coordinates of the heart, as will be described in detail in FIG. 2 below.

The disclosed techniques improve the quality of ablation procedures by assisting the physician in determining ablation locations at both sides of the tissue being ablated, and thereby, forming lesion(s) through the entire thickness of the tissue, and terminating arrhythmias in the patient heart.

System Description

FIG. 1 is a schematic, pictorial illustration of a catheter-based tracking and ablation system 20, in accordance with an example of the present disclosure.

In some examples, system 20 comprises a catheter 22, which is configured to carry out cardiac procedures, and a control console 24. In the example described herein, catheter 22 comprises a focal catheter that may be used for any suitable therapeutic and/or diagnostic purposes, such as sensing electro-anatomical signals and/or ablation of tissue in a heart 26 as will be described in detail hereinafter. In other examples, catheter 22 may comprise any other suitable type of catheter, such as but not limited to a basket catheter, a lasso catheter or a balloon catheter. In the context of the present disclosure and in the claims, the term "ablation" refers to a radiofrequency (RF) ablation procedure or to an irreversible electroporation (IRE) procedure. These procedures are intended to apply one or more high-voltage unipolar or bipolar electrical signals (e.g., pulses) to one or more electrodes in contact with tissue intended to be ablated, so as to form a lesion in one or more intended location (also referred to herein as ablation sites) in heart 26, and thereby to treat arrhythmia in the heart. The lesion formation is described in more detail in FIG. 2 below.

In some examples, console 24 comprises a processor 33, typically a general-purpose computer, with suitable front end and interface circuits for receiving signals via catheter 22 and for controlling the other components of system 20 described herein. Console 24 further comprises a user display 35, which is configured to receive from processor 33 graphical and/or textual display items, such as a map 27 of heart 26, and to display map 27, and optionally several annotations presented over map 27, as shown, for example, in FIG. 2 below.

In some examples, map 27 may comprise any suitable type of three-dimensional (3D) anatomical map produced using any suitable technique. For example, the anatomical map may be produced using an anatomical image produced by using a suitable medical imaging system, or using a fast anatomical mapping (FAM) technique available in a CARTO™ system, produced by Biosense Webster Inc. (Irvine, Calif.), or using any other suitable technique, or using any suitable combination of the above.

In some examples, console 24 comprises a recording unit 38, which is configured to record in case of failure in the CARTO™ system and/or a failure to pace in certain electrode(s). Console 24 comprises a patient interface unit (PIU) 44, which is configured to produce a signal indicative of the location and electrocardiogram (ECG) signals that are acquired and processed and to exchange signals between console 24 and multiple entities (e.g., catheter 22) of system 20.

Reference is now made to an inset 23. In some examples, prior to performing an ablation procedure, a physician 30 inserts one or more catheters through the vasculature system of a patient 28 lying on a table 29, so as to perform electro-anatomical (EA) mapping of tissue in question of heart 26. Based on the EA mapping, physician 30 plans the ablation or IRE procedure, which is carried out using focal catheter 22 or using any other suitable catheter.

Reference is now made to an inset 42. In some examples, catheter 22 comprises a distal-end assembly (DEA) 40 having one or more ablation electrodes 55 configured to apply the ablation signal to the tissue of heart 26. Catheter 22 further comprises a position sensor 39, which is typically coupled to the distal end of catheter 22 and is configured to produce position signals indicative of the measured position of DEA 40, and more specifically, of ablation electrode(s) 55 in an XYZ coordinate system, as will be described in detail hereinafter.

In some examples, DEA 40 comprises a contact force sensor, refers to herein as a force sensor 54, which is configured to measure a force applied by DEA 40 of catheter 22 to the endocardial tissue of heart 26. Force sensor 54 is configured to produce a force signal, which is indicative of the force applied by DEA 40 to the endocardial tissue of heart 26. In some examples, the force sensor may comprise a magnetic field transmitter and receiver connected by a spring in DEA 40, and may generate an indication of the force based on measuring the deflection of the spring. Further details of this sort of catheter and force sensor are described in U.S. Patent Application Publication Nos. 2009/0093806 and 2009/0138007. In other examples, force sensor 54 may comprise any other suitable type of force sensor.

In the present example, ablation electrode 55 is positioned at the tip of DEA 40 and is placed in contact with the endocardial tissue of heart 26, so that the force signal is indicative of the force applied between ablation electrode 55 and the endocardial tissue of heart 26.

Reference is now made back to the general view of FIG. 1. In some examples, PIU 44 is connected to a power source, such as a radiofrequency (RF) generator 49, which is packaged within the housing of PIU 44. In alternative examples, the RF generator may be external to the housing of PIU 44 and electrically connected to PIU 44 using a suitable cable. RF generator 49 is configured to apply suitable RF ablation signals.

In some examples, the proximal end of catheter 22 is connected, inter alia, to interface circuits (not shown) of PIU 44, for transferring the ablation signals from PIU 44 to electrode 55 and applying the ablation signals to tissue of heart 26. The interface circuits are further configured to conduct position signals between position sensor 39 and processor 33.

In some examples, system 20 comprises an indifferent electrode 48, also referred to herein as a patch electrode, which is attached to the skin of patient 28 (e.g., on the backside of patient torso) and is electrically connected to PIU 44 via a cable 21. In other examples, system 20 may comprise any suitable number of skin patches configured to adhere respective electrodes, e.g., about four or five electrodes, to the skin of patient 28.

In the context of the present disclosure and in the claims, the terms "about" or "approximately" for any numerical values or ranges indicate a suitable dimensional tolerance that allows the part or collection of components to function for its intended purpose as described herein.

In some examples, system 20 comprises a handle 32 used by physician 30 to navigate DEA 40 through the vasculature of patient 28 and into a target location for performing the ablation in heart 26.

In some examples, the position of distal-end assembly in the vasculature and heart 26 of patient 28 is measured using position sensor 39 of a magnetic position tracking system. In the present example, console 24 comprises a driver circuit 41, which is configured to drive magnetic field generators 36 placed at known positions external to patient 28 lying on table 29, e.g., below the patient's torso. The position sensor is coupled to the distal end, and is configured to generate position signals in response to sensed external magnetic fields from field generators 36. The position signals, also refers to herein as position measurements, are indicative of the position of DEA 40 in the XYZ coordinate system of the position tracking system.

This method of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publication Nos. 2002/0065455 A1, 2003/0120150 A1 and 2004/0068178 A1.

In some examples, the coordinate system of the position tracking system is registered with the coordinate systems of system 20 and map 27, so that processor 33 is configured to display the position of distal-end assembly over the anatomical or EA map (e.g., map 27).

In some examples, processor 33 is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

This particular configuration of system 20 is shown by way of example, in order to illustrate certain problems that are addressed by examples of the present disclosure and to demonstrate the application of these examples in enhancing the performance of such a system. Examples of the present disclosure, however, are by no means limited to this specific sort of example system, and the principles described herein may similarly be applied to other sorts of catheters and/or medical systems configured to be used for other sorts of tissue ablation procedures.

Figure 2:
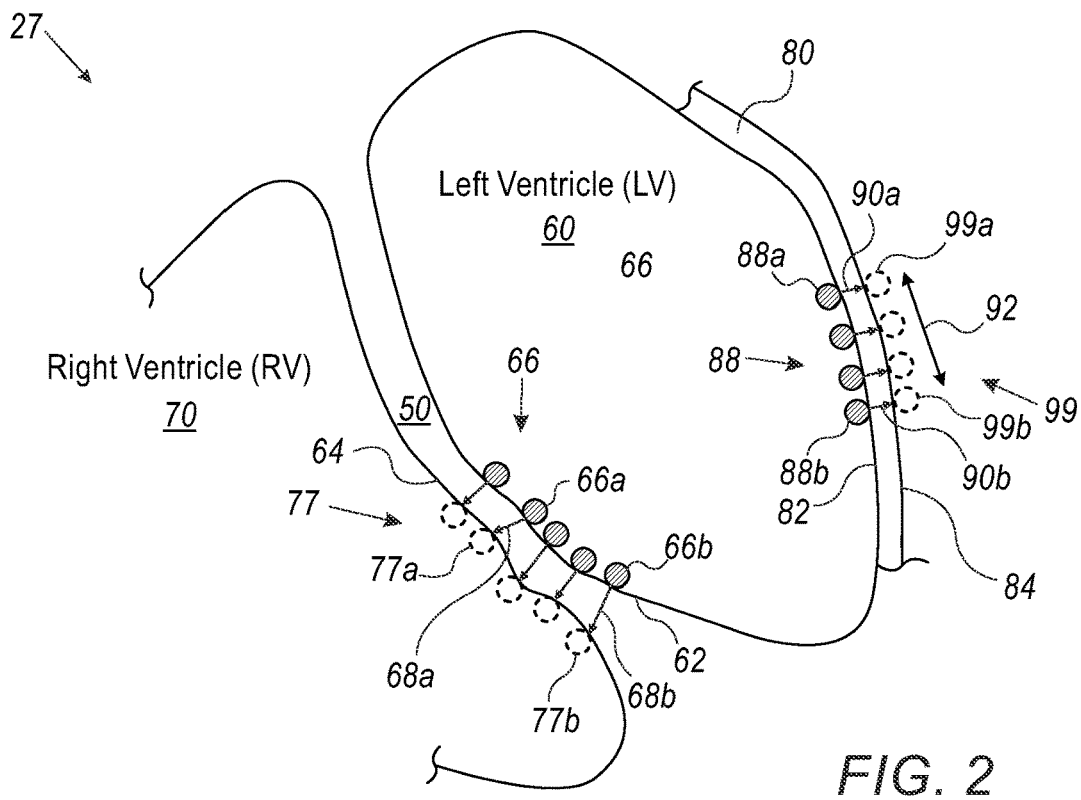
FIG. 2 is a schematic, pictorial illustration of markers indicative of suggested ablation locations, which are displayed on tissue surface and are based on lesions formed on an opposite side of the tissue, in accordance with an example of the present disclosure.

Displaying on Tissue Surface Markers of Suggested Ablation Locations Calculated Based on Lesions Formed on an Opposite Side of the Tissue FIG. 2 is a schematic, pictorial illustration of markers 77 indicative of suggested ablation locations, which are displayed over map 27 on surface 64 of tissue 50 and are based on lesions formed on an opposite surface 62 of tissue 50, in accordance with an example of the present disclosure.

In some cases, physician 30 uses electrode 55 of catheter 22 for applying ablation signals to one side of tissues 50 and 80 of heart 26. In the present example, tissue 50 comprises a septum between a left ventricle (LV) and a right ventricle (RV) 70 of heart 26. Tissue 50 is defined between surfaces 62 and 64, which are the walls of LV 60 and RV 70, respectively. Similarly, tissue 80 comprises a pericardium of heart 26 that is defined between surfaces 82 and 84, which are the endocardium and the epicardium, respectively, of the pericardium.

For example, the ablation signals are applied to surface 82 in order to kill the cells of tissue 80, and thereby, to transform the living cells located between surfaces 82 and 84 of a section 92, to a contiguous lesion. Note that the lesion is intended to be formed through the entire thickness of tissue 80 (between surfaces 82 and 84), so as to block the propagating of one or more electrophysiological (EP) waves through section 92 of tissue 80. In some cases, applying the ablation signals to one side of tissue 80, e.g., to surface 82, is sufficient to form the desired contiguous lesion through the thickness of tissue 80 (i.e., between surfaces 82 and 84) along section 92.

In other cases, however, the lesion formed in response to applying the ablation signals to one side (e.g., to surface 82) is incomplete, and may not fully block EP waves from propagating through section 92 of tissue 80. In such cases, physician 30 must navigate DEA 40 of catheter 22 out of heart 26 for applying additional ablation signals to surface 84 (i.e., the epicardium) at positions that are facing the lesions formed on surface 82 (i.e., the endocardium). Note that due to the three-dimensional (3D) structure of tissue 80, it is difficult to accurately determine the positions intended to be ablated on surface 84.

In some examples, processor 33 is configured to display over map 27, markers 88 indicative of the respective positions in which the ablation signals have been applied to surface 82, and have formed one or more lesions.

In some examples, processor 33 is configured to calculate on surface 84, respective positions that are facing markers 88, typically by projecting the location of markers 88 on surface 84 that is facing surface 82. Based on the projection, processor 33 is configured to display over map 27, markers 99, which are indicative of the calculated positions. In the present example, markers 99 are shown in dashed circles for being suggested locations, which are intended for guiding physician 30 to apply ablation pulses to surface 84, and thereby, to form respective lesions that are facing the lesions formed on surface 82 and are marked by markers 88.

In some examples, processor 33 is configured to calculate a distance 90 between each pair of markers 88 and 99. For example, a distance 90a between markers 88a and 99a, and a distance 90b between markers 88b and 99b. In case physician 30 accepts the suggested ablation locations, and based on the calculated distances, processor 33 and/or physician 30 may determine one or more ablation parameters that will obtain the desired contiguous lesion in section 92 in response to applying the ablation pulses at the positions of markers 99. Note that in the present example, the term "projection" refers to the shortest distance 90 between the respective markers 88 and 99 on surfaces 82 and 84, respectively. In an example, processor 33 is configured to calculate multiple distances between marker 88a and multiple locations on surface 84, and to determine the position of marker 99a based on distance 90a, which is the shortest distance among the calculated distances.

In the example of section 92 of tissue 80, surfaces 82 and 84 are facing one another and are also substantially parallel to one another, and therefore, distances 90a and are approximately equal. In the example of tissue 50, surfaces 62 and 64 are facing one another but are not parallel to one another due to the anatomy of LV 60 and RV Note that in the example of FIG. 2, LV 60 has already been mapped and one or more ablation signals have already been applied to one or more tissues of the walls of LV 60, whereas RV 70 may have not been mapped yet (e.g., using one or more ECG sensing electrodes of catheter 22 or of any other suitable catheter.

In some examples, processor 33 is configured to display over map 27, markers 66 indicative of the respective positions in which the ablation signals have been applied to surface 62. In the present example, the ablation signals applied at the positions of markers 66 have formed in tissue 50 one or more lesions that are incomplete between surfaces 62 and 64. In other words, at least a portion of EP waves may propagate through tissue which is not obtaining the goal of the ablation procedure carried out on tissue 50.

In some examples, processor 33 is configured to calculate on surface 64, respective positions that are facing markers 66, typically by projecting the location of markers 66 on surface 64 that is facing surface 62. Based on the projection, processor 33 is configured to display over map 27, markers 77, which are indicative of the calculated positions. In the present example, markers 77 are shown in dashed circles for being suggested locations, which are intended for guiding physician 30 to apply ablation pulses to surface 64, and thereby, to form respective lesions that are facing the lesions formed on surface 62.

In some examples, processor 33 is configured to calculate a distance 68 between each pair of markers 66 and 77. For example, a distance 68a between markers 66a and 77a, and a distance 68b between markers 66b and 77b. As described for tissue 80 above, if physician 30 accepts the suggested ablation locations shown as markers 77, and based on the calculated distances 68, processor 33 and/or physician 30 may determine for each location marked by a respective marker 77, one or more ablation parameters. In response to applying ablation signals comprising the determined ablation parameters at the positions of markers 99, the desired contiguous lesion is typically formed in the ablated section of tissue 50.

In the example of tissue 50, the term projection refers to the shortest distance 68 between respective pairs of markers 66 and 77 displayed over surfaces 62 and 64, respectively. Note that because in the ablated section surfaces 62 and 64 are not parallel to one another, the orientation and the calculated distance may alter between pairs of markers 66 and 77.

For example, the size of distance 68a and the orientation of the arrow marking distance 68a differs from that of distance 68b. Therefore, physician 30 may decide to: (i) use different ablation parameters in ablation signals applied to surface 64 at the positions of markers 77a and 77b, and (ii) direct DEA 40 in different directions, e.g., in the locations of markers 77a and 77b, so the to obtain a contiguous lesion in the ablated section between surfaces 62 and 64. As described above, the transformation of tissue 50 to the contiguous lesion between surfaces 62 and 64 is intended to block the propagation of EP waves through the septum between LV 60 and RV 70, and thereby, to treat arrhythmia in heart 26.

In some examples, when implementing the techniques described above, at least one of markers 77 and 99 are displayed over map 27, and are used for assisting physician to navigate DEA 40 to the positions marked by the displayed markers. As described in FIG. 1 above, based on position signals of position sensor 39, processor 33 is configured to continuously display over map 27 a given marker (not shown) indicative of the position of DEA 40 in heart 26. In such examples, physician 30 moves catheter 22 in order to position DEA 40 at one or more of at the suggested ablation locations, and subsequently, controls catheter 22 to apply the predefined ablation signals to the tissue at the suggested positions. For example, when the position of the given marker is merged with the position of marker 77a, physician 30 may control catheter 22 to apply the ablation signals in order to form a contiguous lesion between surfaces 62 and 64, at least between the positions of markers 66a and 77a.

In other examples, catheter 22 comprises a basket catheter (not shown) having multiple ablation electrodes (not shown). In such examples, physician 30 moves catheter 22 so that the positions of multiple electrodes of DEA 40 are merged with the respective positions of markers 77, and subsequently, physician 30 may control catheter 22 to apply the ablation signals (using the respective ablation electrodes 55) to surface 64 at the positions marks by markers 77, in order to form the contiguous lesion between surfaces 62 and 64.

The configuration of markers 66, 77, 88 and 99, and of distances 68 and 90, are shown by way of example for the sake of conceptual clarity, and in other examples, processor 33 is configured to use any other suitable calculation for determining: (i) the position of one or more of these markers and/or distances, and (ii) the size, shape and other parameters related to the appearance of any suitable type of markers for assisting physician 30 in determining the ablation of one or both tissues 50 and 80. For example, at least one of distances 68 and 90 may be presented as textual figures, e.g., in a table presented over map 27.

Note that in the example of FIG. 2, the surfaces of tissues 50 and 80 are facing one another and are in physical contact with fluids within and surrounding heart 26. For example, surfaces 62 and 64 are facing one another and are in physical contact with blood flowing through LV 60 and RV 70. Similarly, surfaces 82 and 84 are facing one another and surfaces 82 is in physical contact with blood flowing through LV 60 and surface 84 is in physical contact with fluids surrounding heart 26. In other examples, at least one of surfaces 62, 64, 82 and 84 may be accessible to DEA 40 though the vasculature of patient 28 and/or through other (soft or hard) tissues of the patient, so as to apply the techniques described above.

Figure 3:
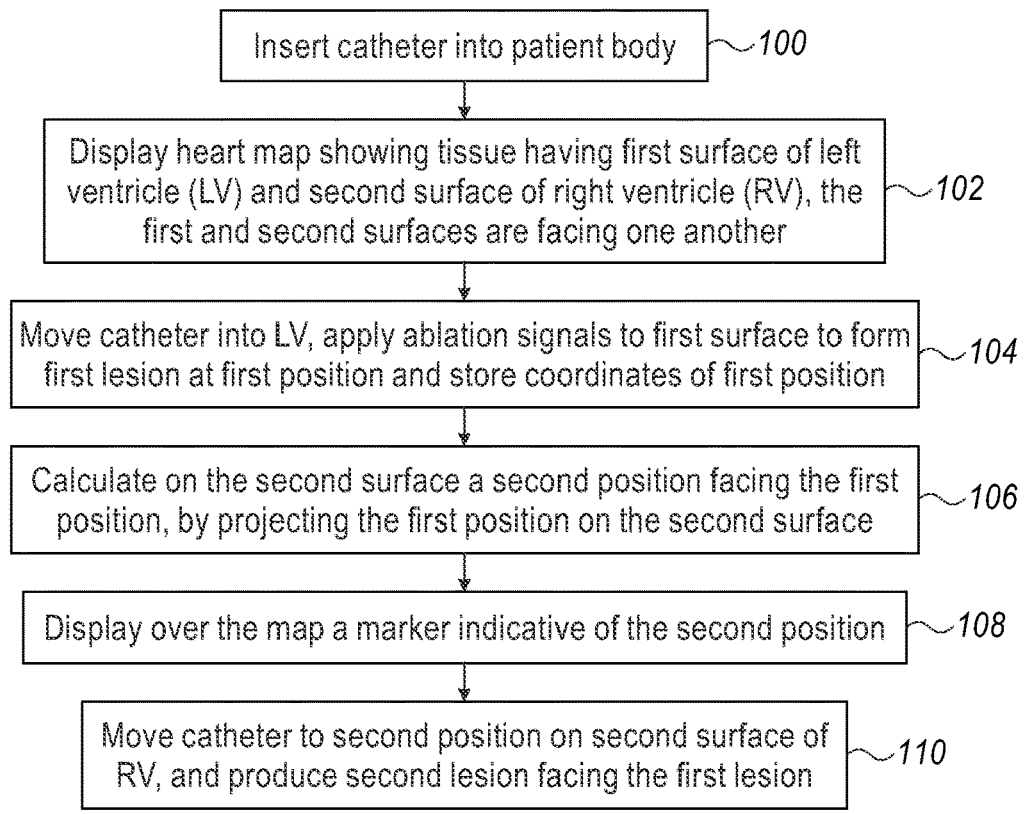
FIG. 3 is a flow charts that schematically illustrate a method for displaying on tissue surface markers of suggested ablation locations that are calculated based on lesions formed on an opposite side of the tissue, in accordance with an example of the present disclosure.

FIG. 3 is a flow charts that schematically illustrate a method for displaying on surface 64 of tissue 50, markers 77 indicative of suggested ablation locations that are calculated based on lesions formed on surface 62 of tissue in accordance with an example of the present disclosure.

The method begins at a catheter insertion step 100, with physician 30 inserting DEA 40 of catheter 22 into the body of patient 28, as described in FIGS. 1 and 2 above.

At a heart map displaying step 102, processor 33 displays map 27 showing tissue 50 having surface 62 of left ventricle (LV) 60 and surface 64 of right ventricle (RV) which are facing one another, as described in FIG. 2 above.

At a first ablation step 104, physician 30 moves catheter 22 into LV, controls system 20 to apply ablation signals to surface 62 so as to form first lesion at one or more first positions on surface 62, and processor 33 stores the coordinates of the one or more first position. In the example of FIG. 2 above, processor 33 displays the first positions over surface 62 using markers 66.

At a calculation step 106, processor 33 calculates on surface 64 one or more second positions facing the respective one or more first positions, by projecting the one or more first positions on surface 64, as described in detail in FIG. 2 above.

At a marker displaying step 108, processor 33 displays over map 27 one or more markers 77 indicative of the one or more second positions on surface 64, and distances 68 between respective pairs of the first and second positions. In the example of FIG. 2, distances 77 are displayed between markers 66 and 77 located on surfaces 62 and 64, respectively.

At a second ablation step 110 that terminates the method, physician 30 moves catheter 22 into RV 70 for positioning DEA 40 at the second positions shown by markers 77. In the present example, catheter 22 comprises a focal catheter, and therefore, physician 30 (i) moves DEA 40 sequentially to each of the second positions so that the position of ablation electrode 55 merges with the position of each marker 77, and (ii) produces multiple second lesions (that are facing the first lesions shown as markers 66) at the respective positions of markers 77, as described in detail in FIG. 2 above.

In some examples, physician 30 may carry out a test to confirm the formation of a contiguous lesion that blocks the propagation of EP waves through tissue 30, which is the septum between LV 60 and RV 70.

In some examples, the method of FIG. 3 is applicable, mutatis mutandis, for producing a contiguous lesion along section 92 between surfaces 82 and 84, as described in detail in FIG. 2 above.

In some examples, after obtaining and verifying the formation of one or more contiguous lesion at the locations intended to be ablated, physician 30 may extract catheter 22 out of the body of patient 28.

Although the examples described herein mainly address electrophysiology procedures (such as but not limited to RF ablation and/or IRE procedures) carried out in patient heart 26, the methods and systems described herein can also be used in other applications, such as in any catheterization procedure carried out on both sides of tissue in any suitable organ of a patient.

Examples 1

A system (20) includes a display (35) and a processor (33). The display (35) is configured to display at least a map (27) of an organ (26) having tissue (50) including first and second surfaces (62, 64) that are facing one another. The processor (33) is configured to: (i) receive a first position (66) of a first lesion formed by ablating the first surface (62), (ii) calculate, on the second surface (64), a second position that is facing the first position (66), and display, over the map (27), a marker (77) indicative of the second position for guiding a user (30) to produce in the tissue (50) a second lesion facing the first lesion.

Example 2

The system according to Example 1, wherein the processor is configured to calculate the second position by: (a) selecting two or more locations on the second surface, (b) calculating two or more distances, respectively, between: (i)

the first position and (ii) each of the two or more locations, and (iii) selecting the second position from among the two or more locations, based on a shortest distance selected among the two or more distances.

Example 3

The system according to Example 1, wherein the processor is configured to calculate the second position by computing a projection of the first position on the second surface.

Example 4

The system according to Example 1, wherein the processor is configured to display over the map an additional marker indicative of the first lesion.

Example 5

The system according to Examples 1 through 4, wherein the processor is configured to display over the map a distance between the first and second positions.

Example 6

The system according to Example 5, wherein, based on the distance, the processor is configured to set one or more ablation parameters for producing the second lesion.

Example 7

The system according to Example 6, wherein the processor is configured to set the one or more ablation parameters for transforming the tissue between the first and second positions into a contiguous lesion including the first and second lesions.

Example 8

The system according to Examples 1 through 4, wherein the organ includes a heart, and wherein at least one of the first and second surfaces includes an endocardium or an epicardium of the heart.

Example 9

The system according to Examples 1 through 4, wherein one or both of the first and second surfaces are facing fluids that are located at one or both of: (i) within the organ, and (ii) surrounding the organ.

Example 10

The system according to Example 9, wherein the organ includes a heart, wherein the first and second surfaces include first and second walls of first and second cavities of the heart, respectively, and wherein the fluids include blood being pumped through the first and second cavities.

Example 11

A method, including:
  displaying at least a map (27) of an organ (26) having tissue (50) including first and second surfaces (62, 64) that are facing one another;
  receiving a first position (66) of a first lesion formed by ablating the first surface (62);
  calculating, on the second surface (64), a second position that is facing the first position; and
  displaying, over the map (27), a marker (77) indicative of the second position for guiding a user (30) to produce in the tissue (50) a second lesion facing the first lesion.

Example 12

The method according to claim Example 11, wherein calculating the second position comprising: (a) selecting two or more locations on the second surface, (b) calculating two or more distances, respectively, between: (i) the first position and (ii) each of the two or more locations, and (iii) selecting the second position from among the two or more locations, based on a shortest distance selected among the two or more distances.

Example 13

The method according to Example 11, wherein calculating the second position comprises computing a projection of the first position on the second surface.

Example 14

The method according to Example 11, and comprising displaying over the map an additional marker indicative of the first lesion.

Example 15

The method according to any of Examples 11 through 14, and comprising displaying over the map a distance between the first and second positions.

Example 16

The method according to Example 15, and comprising setting one or more ablation parameters based on the distance for producing the second lesion.

Example 17

The method according to Example 16, wherein the one or more ablation parameters are set for transforming the tissue, between the first and second positions, into a contiguous lesion comprising the first and second lesions.

Example 18

The method according to Examples 11 through 14, wherein the organ comprises a heart, and wherein at least one of the first and second surfaces comprises an endocardium or an epicardium of the heart.

Example 19

The method according to Examples 11 through 14, wherein one or both of the first and second surfaces are facing fluids that are located at one or both of: (i) within the organ, and (ii) surrounding the organ.

Example 20

The method according to Example 19, wherein the organ comprises a heart, wherein the first and second surfaces comprise first and second walls of first and second cavities of the heart, respectively, and wherein the fluids comprise blood being pumped through the first and second cavities.

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for providing ablation guidance, comprising:
   a display, which is configured to display at least a three-dimensional (3D) anatomical map of an organ having tissue comprising first and second surfaces that are facing one another; and
   an ablation catheter for forming a first lesion on the tissue, by applying ablation signals to the first surface of the tissue;
   a processor, which is configured to:
      receive a first position of the first lesion formed by the ablation catheter ablating the first surface;
      calculate, on the second surface, a second position that is facing the first position by: (a) selecting two or more locations on the second surface, (b) calculating two or more distances, respectively, between: (i) the first position and (ii) each of the two or more locations, and (iii) selecting the second position from among the two or more locations, based on a shortest distance selected among the two or more distances;
      determine the calculated second position to be a position for a marker, based on the selected shortest distance; and
      display, over the 3D anatomical map, the marker indicative of the second position, for guiding a user to produce on the second surface of the tissue a second lesion facing the first lesion by applying ablation signals to the second surface of the tissue.

2. The system according to claim 1, wherein the processor is configured to calculate the second position by computing a projection of the first position on the second surface.

3. The system according to claim 1, wherein the processor is configured to display over the map an additional marker indicative of the first lesion.

4. The system according to claim 1, wherein the processor is configured to display over the map a distance between the first and second positions.

5. The system according to claim 4, wherein, based on the distance, the processor is configured to set one or more ablation parameters for producing the second lesion.

6. The system according to claim 5, wherein the processor is configured to set the one or more ablation parameters for transforming the tissue between the first and second positions into a contiguous lesion comprising the first and second lesions.

7. The system according to claim 1, wherein the organ comprises a heart, and wherein at least one of the first and second surfaces comprises an endocardium or an epicardium of the heart.

8. The system according to claim 1, wherein one or both of the first and second surfaces are facing fluids that are located at one or both of: (i) within the organ, and (ii) surrounding the organ.

9. The system according to claim 8, wherein the organ comprises a heart, wherein the first and second surfaces comprise first and second walls of first and second cavities of the heart, respectively, and wherein the fluids comprise blood being pumped through the first and second cavities.

10. A method for providing ablation guidance, comprising:
    displaying at least a three-dimensional (3D) anatomical map of an organ having tissue comprising first and second surfaces that are facing one another;
    forming a first lesion on the tissue, by applying ablation signals by an ablation catheter to the first surface of the tissue;
    receiving a first position of the first lesion formed by the ablation catheter ablating the first surface;
    calculating, on the second surface, a second position that is facing the first position by: (a) selecting two or more locations on the second surface, (b) calculating two or more distances, respectively, between: (i) the first position and (ii) each of the two or more locations, and (iii) selecting the second position from among the two or more locations, based on a shortest distance selected among the two or more distances;
    determining the calculated second position to be a position for a marker, based on the selected shortest distance; and
    displaying, over the 3D anatomical map, the marker indicative of the second position for guiding a user to produce on the second surface of the tissue a second lesion facing the first lesion by applying ablation signals to the second surface of the tissue.

11. The method according to claim 10, wherein calculating the second position comprises computing a projection of the first position on the second surface.

12. The method according to claim 10, and comprising displaying over the map an additional marker indicative of the first lesion.

13. The method according to claim 10, and comprising displaying over the map a distance between the first and second positions.

14. The method according to claim 13, and comprising setting one or more ablation parameters based on the distance for producing the second lesion.

15. The method according to claim 14, wherein the one or more ablation parameters are set for transforming the tissue, between the first and second positions, into a contiguous lesion comprising the first and second lesions.

16. The method according to claim 10, wherein the organ comprises a heart, and wherein at least one of the first and second surfaces comprises an endocardium or an epicardium of the heart.

17. The method according to claim 10, wherein one or both of the first and second surfaces are facing fluids that are located at one or both of: (i) within the organ, and (ii) surrounding the organ.

18. The method according to claim 17, wherein the organ comprises a heart, wherein the first and second surfaces comprise first and second walls of first and second cavities of the heart, respectively, and wherein the fluids comprise blood being pumped through the first and second cavities.

* * * * *